United States Patent [19]

Grosvenor et al.

[11] Patent Number: 4,768,509

[45] Date of Patent: Sep. 6, 1988

[54] SURGICAL KNIFE

[75] Inventors: Kenneth R. Grosvenor, Hitchin; David B. Waldock, Brentwood, both of United Kingdom

[73] Assignees: Duckworth & Kent Surgical Instruments Limited, Hertfordshire, England; Medical Titanium Corporation, Clearwater, Fla.

[21] Appl. No.: 937,168

[22] Filed: Dec. 2, 1986

[30] Foreign Application Priority Data

Dec. 7, 1985 [GB] United Kingdom ............... 8530210

[51] Int. Cl.$^4$ ............................................. A61B 17/32
[52] U.S. Cl. .................................... 128/305; 30/335
[58] Field of Search ............... 128/305, 305.3, 307, 128/311, 314, 315, 329 R, 329 A, 330; 604/117, 119; 30/335, 162

[56] References Cited

U.S. PATENT DOCUMENTS

| 253,185 | 2/1882 | Christmiller | 30/162 |
| 2,857,912 | 10/1958 | Feinstone et al. | 604/199 |
| 3,307,551 | 3/1967 | Violet, Jr. | 128/305.3 |
| 4,473,076 | 9/1984 | Williams et al. | 128/305 |
| 4,499,898 | 2/1985 | Knepshield et al. | 128/305 |
| 4,534,348 | 8/1985 | Fedorov et al. | 128/305 |

FOREIGN PATENT DOCUMENTS 2113550 6/1985 United Kingdom .

Primary Examiner—Dalton L. Truluck
Assistant Examiner—Denise Whelton
Attorney, Agent, or Firm—Seidel, Gonda, Goldhammer & Abbott

[57] ABSTRACT

A surgical knife, particularly for use in radial keratotomy, comprises a blade, such as a diamond, which is movable for adjustment of the depth of cut by an invariant coupling to a micrometer mechanism, without provision for full retraction of the blade, and a removable protective end cap adapted to encompass the blade when the knife is not in use. The invariant coupling of the blade to the micrometer mechanism is via a mechanical linkage which incorporates a rotatable spindle having two axially separate screw-thread connections. The end cap is provided with holes for the passage of sterilizing fluid to and around the blade.

6 Claims, 3 Drawing Sheets

SURGICAL KNIFE

FIELD OF THE INVENTION

This invention relates to surgical knives, and is particularly concerned with surgical knives for use in radial keratotomy. In radial keratotomy it is important that the extent to which the cutting blade projects beyond the guard should not only be accurate, but also accurately repeatable. The incisions made by the surgeon are very shallow, but must be extremely accurate in terms of the depth of cut.

It is known to provide a surgical knife, suitable for radial keratotomy, which incorporates a micrometer mechanism. However, such knives which incorporate a micrometer mechanism also incorporate a retraction mechanism whereby the cutting blade can be retracted back into the knife, after use, in order to protect the cutting blade. This has been considered necessary because the modern diamond blade is relatively fragile and therefore needs to be protected when undergoing sterilisation in an autoclave for example. However, any knife which has a retraction mechanism built into it will have an inherent error factor. With the known knives of this type it is possible to have quite a large variation in the cutting depth of the blade even with an apparently consistent adjustment of the micrometer mechanism. For example, with the known knives, variations of up to 30 microns in the position of the blade in relation to the footplate have been found following just one advance and retraction movement. There is little or no advantage in being able to adjust the position of the cutting blade by means of a micrometer mechanism to within a few microns if the repeatability of the setting cannot be guaranteed.

SUMMARY OF THE INVENTION

It is therefore an object of the present invention to provide a surgical knife in which the cutting depth of the blade is as accurate as the accuracy of the micrometer mechanism itself. By this means, with the knife in accordance with the present invention, once the knife is calibrated then it will remain accurate without any need for further calibration or adjustment.

It is a further object of the present invention to provide a surgical knife appropriate for radial keratotomy in which there is an invariant connection between the micrometer mechanism and the cutting blade itself.

In accordance with one aspect of the present invention there is provided a surgical knife comprising a blade which is movable for adjustment of the depth of cut by an invariant coupling to a micrometer mechanism, without provision for full retraction of the blade, and removable protective means adapted to encompass the blade when the knife is not in use.

In accordance with another aspect of the invention there is provided a surgical knife comprising a generally cylindrical knife body, a blade arranged to be mounted for forward and rearward depth-of-cut adjustment displacement only, depth-of-cut setting means towards the rearward end of the body, coupling means providing an invariant mechanical linkage between said setting means and the blade whereby movement of the setting means is translated into axial displacement of the blade, and removable protective means adapted to encompass the blade when the knife is not in use.

With the knife of the present invention, because there is no retraction movement built into it, it is necessary to use a removable protective means, such as a cap, on the front end of the knife in order to protect the cutting element. When the knife has been used and is ready to be sterilised then the cap is put on in order to protect the cutting element, e.g. a diamond, during the sterilisation process.

Preferably, the knife incorporates two axially separated screw threads, the combination of which provides for the adjustment setting of the blade depth.

BRIEF DESCRIPTION OF THE DRAWINGS

In order that the invention may be fully understood, one presently preferred embodiment of surgical knife in accordance with the invention will now be described by way of example and with reference to the accompanying drawings.

In the drawings.

DESCRIPTION OF THE PREFERRED EMBODIMENT

Figure 12:
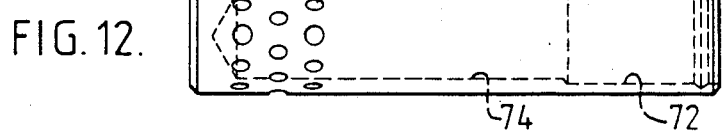

Referring now to the drawings, the surgical knife which is shown therein and which is particularly suitable for radial keratotomy is made substantially entirely of titanium or titanium alloy. The exception is the end cap which is shown in FIG. 12 and which is preferably made of a rigid plastics material.

Figure 1:
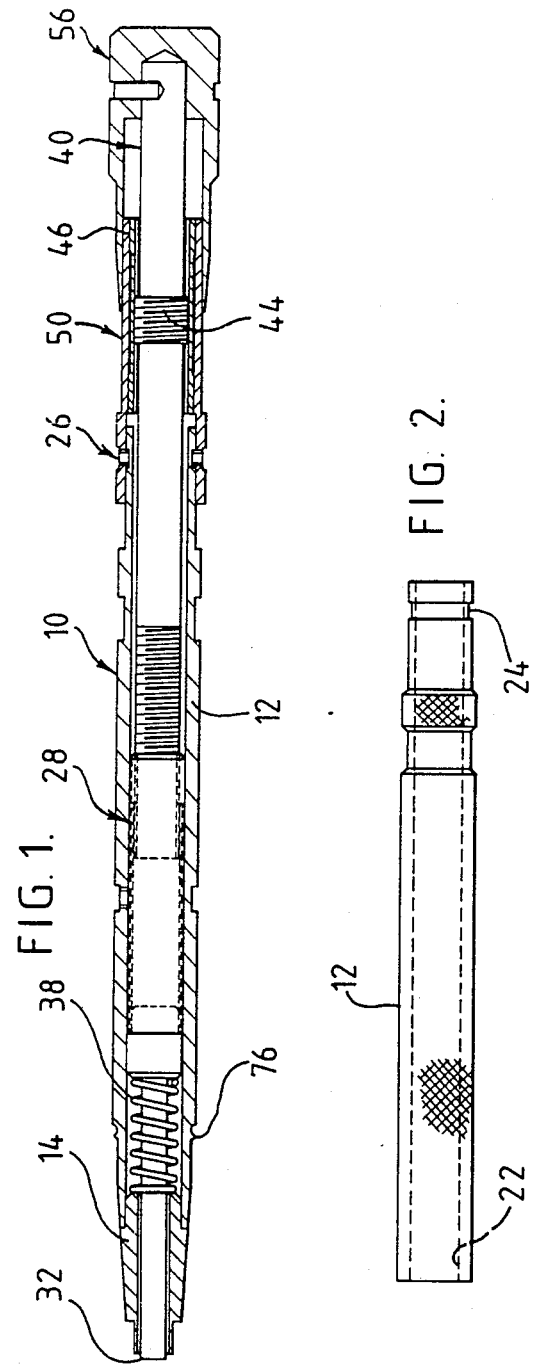
FIG. 1 is a general assembly view of the knife, partly in section, but without the front end cap and guard.
Figure 2:
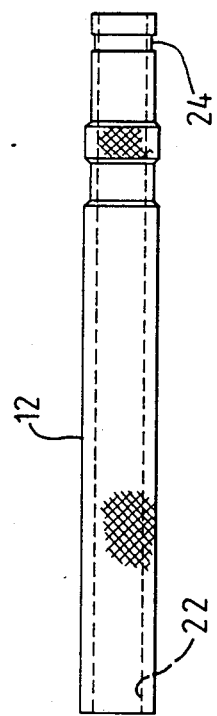
FIG. 2 shows the body of the knife of FIG. 1.
Figure 3:
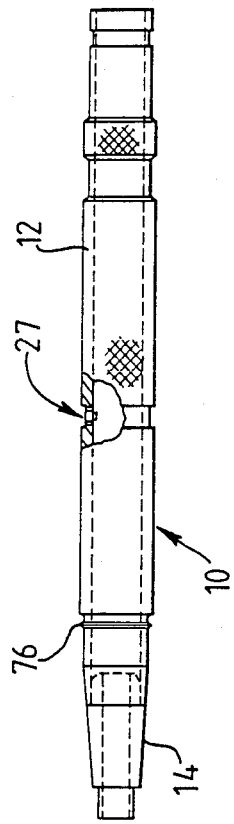
FIG. 3 shows the body assembly of the knife of FIG. 1, comprising the body, a nose and a guide pin.
Figure 4:
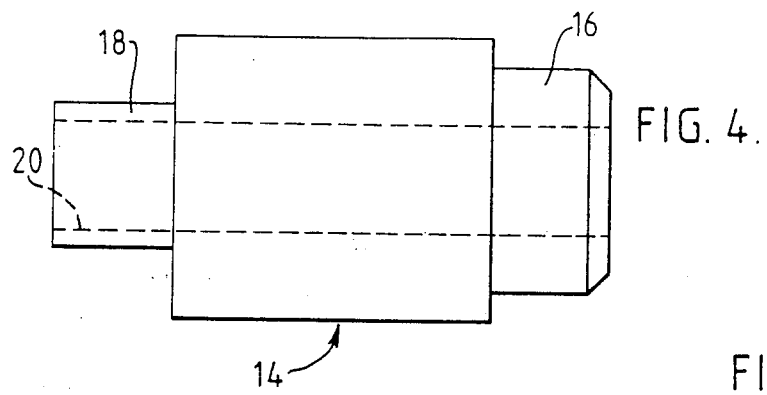
FIG. 4 shows the nose of the body assembly shown in FIG. 3.
Figure 6:
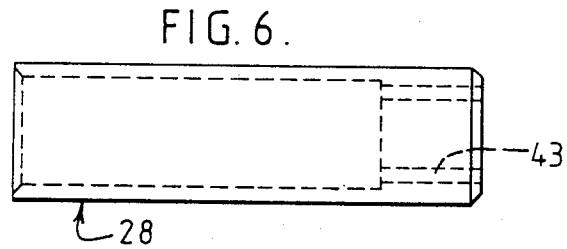
FIG. 6 shows the minor thread bush of the knife.

The knife comprises a generally cylindrical body assembly 10, which is shown in FIG. 3, and which itself comprises a body 12, shown in FIG. 2, and a nose 14, which is also shown in FIG. 4. The nose 14 has a rearwardly projecting stub portion 16 which is a push fit into the open front end of the body 12. The forward end of the nose 14 is provided with a projecting, reduced diameter portion 18, and the nose 14 has a bore 20 extending therethrough. As can be seen from FIGS. 1 and 3, the center section of the nose 14 is tapered at its sides. The body 12 similarly has a bore 22 extending therethrough. The surface of the body 12 is knurled. At the rear end of the body 12 the knurl is removed in part, as shown most clearly in FIG. 2. Towards the rear end of the body 12 there is a circumferential recess 24 in the body surface for the location of two locking screws 26 (FIG. 1) whose function will be apparent later. Approximately mid-way along the length of the body 12, as shown most clearly in FIG. 3, a guide pin 27 extends radially through the body wall and is seated within a circumferential recess formed in the body. This guide pin 27 engages with a groove in a female minor thread bush of the micrometer mechanism, this minor thread bush being indicated at 28 and being shown in detail in FIG. 6.

Figure 5:
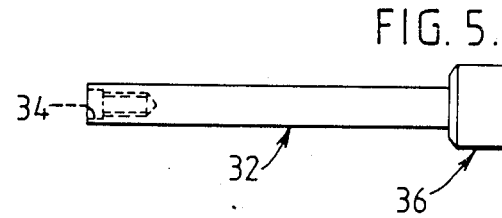
FIG. 5 shows the center rod of the knife.

The forward end of the minor thread bush 28 receives in its open front end a stub 30 of a center rod which is indicated generally at 32 and which is shown in detail in FIG. 5. The center rod 32 extends axially through the nose 14 and is provided with a drilled and tapped hole 34 at its front end. The center rod 32 also includes a cylindrical portion 36 which is a sliding fit within the bore 22 of the body 12. A spring 38 (FIG. 1) is seated at one end against the rearward end face of the nose 14 and at the other end against the forward end face of the cylindrical portion 36 of the center rod, thereby to urge the center rod 32 rearwardly and to take up any play in the internal mechanism of the knife.

Figure 7:
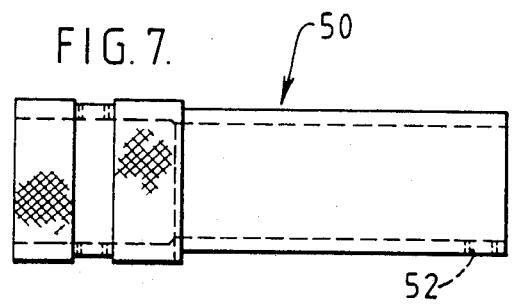
FIG. 7 shows the barrel of the knife.
Figure 8:
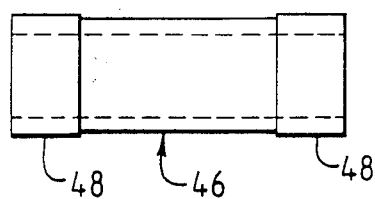
FIG. 8 shows a plug which is fitted within the barrel of FIG. 7.
Figure 9:
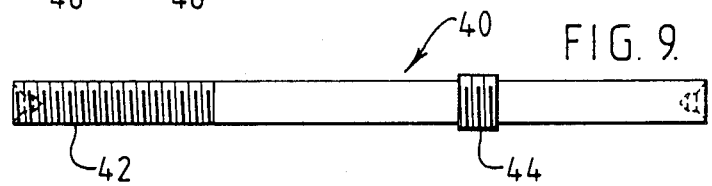
FIG. 9 shows a spindle which extends through the plug of FIG. 8.

The minor thread bush 28 is movable axially within the body 10 and at its rear end receives the forward end of a spindle 40, which is shown in FIG. 9. The forward end of the spindle 40 is provided with an external screw thread 42 which engages with an internal screw thread 43 at the rear end of the minor thread bush 28. The spindle 40 extends rearwardly beyond the body 10 of the knife and is provided, part-way along its length, with a short, externally screw-threaded portion 44. The screw-threaded portion 44 of the spindle 40 is in engagement within a mating plug 46 which is shown in FIG. 8. The plug 46 has two end portions 48 which stand slightly proud of the center section. The plug 46 is housed within a barrel 50 which is shown in detail in FIG. 7. The barrel 50 is provided with three drilled and tapped holes 52 towards its rear end, to permit the plug and barrel to be secured to each other against relative rotation. The forward end of the barrel 50 overlies the rear end of the body 12, as shown most clearly in FIG. 1, and the two locking screws 26 are set into the forward end of the barrel 50, through the wall thereof, to engage with the body 12 and to prevent rotation of the barrel 50 relative to the nose 14. The outer surface of the barrel 50 is provided with axially spaced engraved markings which form one part of the micrometer setting scale.

Figure 10:
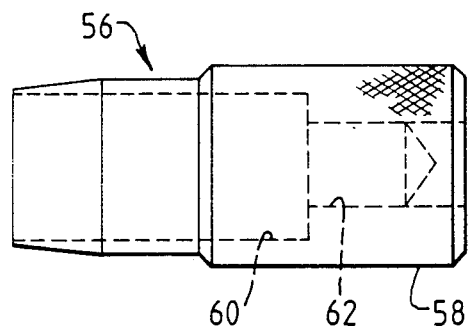
FIG. 10 shows a thimble which is fitted to the end of the spindle of FIG. 9.

Over the rear end of the barrel 50 there is fitted a thimble 56 which isshown most clearly in FIG. 10. The thimble 56 is provided with a fine diamond knurl on its largest diameter, rear end portion 58. The rearward end of the spindle 40 extends rearwardly of the barrel 50 and plug 46 and into a bore 60 and counter-bore 62 within the thimble 56, where it is secured so that rotation of the thimble 56 will cause the spindle 40 to rotate. The outer surface of the forward end of the thimble 56 is provided with circumferentially spaced axial line markings which form the other part of the micrometer setting scale.

It will thus be appreciated that with the micrometer mechanism of the knife of the present invention there is an invariant coupling from the thimble 56 right through to the center rod 32. It is further to be noted that with the knife of the present invention the two screw threads 42,43 and 44,46 which provide for the adjustment of the blade depth are axially separated one from the other. The one screw thread connection is between the forward end of the spindle 40 and the rearward end of the minor thread bush 28, whereas the other screw thread connection is between the threaded portion 44 of the spindle 40 and the plug 46.

Figure 11A:
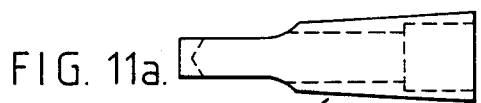
FIGS. 11a and 11b are side and plan views respectively of a straight guard adapted to be fitted to the body assembly of the knife after final assembly; and, FIG. 12 shows an end cap adapted to be fitted over the guard and blade.
Figure 11B:
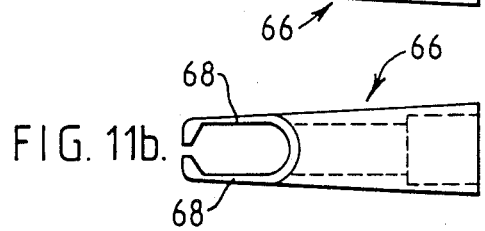

At the forward end of the knife, a diamond blade (not shown) is fitted into a suitable holder (not shown) and the holder is secured into the hole 34 at the forward end of the center rod 32. The diamond blade is protected by a guard 66 which is shown in FIGS. 11a and 11b. This guard 66 has two legs 68 which lie one on each side of the blade. Small adjustments made at the rear end of the knife through the micrometer mechanism, either to increase the depth of cut or to decrease the depth of cut, are transmitted through the center rod 32 to the blade so that the amount by which the blade projects beyond the forward end of the guard 66 can be set to the required value.

Because with the knife of the present invention there is no retraction mechanism by which the blade can be withdrawn into the guard to protect the blade when the knife is not being used by the surgeon, and particularly when the knife is to be sterilised, a substantially cylindrical end cap 70 (FIG. 12) is provided. The end cap 70 is provided with a bore 72 at its rearward end, and with a counterbore 74. As will be seen from FIG. 3 in particular, the body of the knife is provided towards its forward end with a peripheral rib 76 which is engageable with an undercut groove 78 formed within the bore 72 at the rear end of the cap 70. In other words, the end cap is a push fit over the guard 66 and nose 14 of the knife and snaps into place by engagement of the rib 76 and groove 78. The forward end of the cap 70, in the region where the diamond blade will lie when the cap is fitted into place on the knife, is provided with a plurality of holes 80 spaced around its circumference. These holes 80 permit sterilisation of the blade to take place, for example in an autoclave, when the blade is within the protective cap 70. Although the cap 70 is shown as a push fit on to the body of the knife, it could alternatively be designed to be a screw fit on to the knife body.

We claim:

1. A surgical knife comprising:
   a generally cylindrical knife body;
   a blade movable for adjustment of the depth of cut;
   longitudinally extending rod means within the knife body and carrying the blade at a forward end thereof, said rod means being axially displaceable within the knife body but not rotatable relative thereto;
   a coupling member within the knife body connected to said rod means at a forward end of the coupling member for joint axial movement therewith;
   a longitudinally extending rotatable spindle within the knife body, a forward end of the spindle having first thread means in engagement with the rearward end of said coupling member to constitute a first part of a micrometer adjustment mechanism;
   second thread means on said spindle axially separated from said first thread means and providing a threaded connection with said knife body to constitute a second part of the micrometer adjustment mechanism;
   manual setting means for the micrometer adjustment mechanism at the end of the knife body opposite to the blade;
   and removable protective means encompassing the blade;
   the interconnection of the parts within the knife body being arranged to impart movement to the blade only as a result of setting of the micrometer adjustment mechanism and to translate a rotational movement of the setting means directly into rotation of the spindle and thence into axial movement of said coupling member, said rod means and said blade.

2. A surgical knife according to claim 1, in which the spindle is secured to its rearward end to the setting means for rotation therewith, and said second thread means is provided at a position on the spindle axially spaced from each end of the spindle.

3. A surgical knife according to claim 1, in which said coupling member is tubular, having internal thread means at one end thereof in engagement with said first thread means, and having said rod means inserted into the other end thereof.

4. A surgical knife according to claim 1, which includes spring means urging said rod and said coupling member in a direction away from the blade.

5. A surgical knife according to claim 1, in which said protective means comprises a detachable cap of substantially cylindrical configuration.

6. A surgical knife according to claim 1, in which said protective means comprises a cap provided with a plurality of circumferentially spaced holes therethrough positioned so that they are aligned with the blade.

* * * * *